(12) United States Patent
Kim et al.

(10) Patent No.: US 10,364,293 B2
(45) Date of Patent: Jul. 30, 2019

(54) POLYPEPTIDE BINDING TO EXTRACELLULAR DOMAIN OF EPIDERMAL GROWTH FACTOR RECEPTOR

(71) Applicant: KOREA ADVANCED INSTITUTE OF SCIENCE AND TECHNOLOGY, Daejeon (KR)

(72) Inventors: Hak-Sung Kim, Daejeon (KR); Joong-Jae Lee, Daejeon (KR)

(73) Assignee: KOREA ADVANCED INSTITUTE OF SCIENCE AND TECHNOLOGY, Daejeon (KR)

(*) Notice: Subject to any disclaimer, the term of this patent is extended or adjusted under 35 U.S.C. 154(b) by 0 days.

(21) Appl. No.: 15/310,585

(22) PCT Filed: May 21, 2015

(86) PCT No.: PCT/KR2015/005079
§ 371 (c)(1),
(2) Date: Nov. 11, 2016

(87) PCT Pub. No.: WO2015/178689
PCT Pub. Date: Nov. 26, 2015

(65) Prior Publication Data
US 2017/0081422 A1    Mar. 23, 2017

(30) Foreign Application Priority Data
May 23, 2014    (KR) .................. 10-2014-0062391

(51) Int. Cl.
  C07K 14/46     (2006.01)
  C07K 14/71     (2006.01)
  C12N 15/62     (2006.01)
  C07K 14/195    (2006.01)
  C12P 21/02     (2006.01)
  C07K 16/30     (2006.01)
  C07K 19/00     (2006.01)

(52) U.S. Cl.
  CPC ............ *C07K 16/30* (2013.01); *C07K 14/195* (2013.01); *C07K 14/46* (2013.01); *C07K 14/71* (2013.01); *C07K 19/00* (2013.01); *C12N 15/62* (2013.01); *C12P 21/02* (2013.01); *C07K 2318/20* (2013.01)

(58) Field of Classification Search
None
See application file for complete search history.

(56) References Cited

FOREIGN PATENT DOCUMENTS

| KR | 10-2006-0017585 A | 2/2006 |
| KR | 101219628 A | 1/2013 |
| KR | 10-2013-0098089 A | 9/2013 |

OTHER PUBLICATIONS

Bella, J., et al., "The Leucine-Rich Repeat Structure", "Cellular and Molecular Life Sciences", Apr. 14, 2008, pp. 2307-2333, vol. 65.
Lee, S., et al, "Design of a Binding Scaffold Based on Variable Lymphocyte Receptors of Jawless Vertebrates by Module Engineering", "Proceedings of the National Academy of Sciences", Feb. 28, 2012, pp. 3299-3304, vol. 109, No. 9.

*Primary Examiner* — Christina Bradley
(74) *Attorney, Agent, or Firm* — Hultquist, PLLC; Steven J. Hultquist

(57) ABSTRACT

The present invention relates to a polypeptide capable of binding specifically to the extracellular domain of epidermal growth factor receptor, a polynucleotide that encodes the polypeptide, an expression vector comprising the polynucleotide, a recombinant microorganism having the expression vector introduced therein, and a method of producing the polypeptide using the recombinant microorganism. The polypeptide according to the present invention can bind to the extracellular domain of epidermal growth factor receptor with a high binding affinity comparable to those of existing monoclonal antibodies that are widely used as targeted therapeutic agents, thereby inhibiting the activity of the epidermal growth factor receptor. The polypeptide is useful for the development of agents for the prevention or diseases associated with overexpression of epidermal growth factor receptor.

11 Claims, 6 Drawing Sheets
(5 of 6 Drawing Sheet(s) Filed in Color)
Specification includes a Sequence Listing.

Table List of the sequences of selected repebodies

| Group | Module 3 | | | Module 4 | | | # of clones |
|---|---|---|---|---|---|---|---|
| | I126 | T128 | G129 | V150 | V152 | E153 | |
| A | Met | His | Tyr | Tyr | Ser | Glu | 12 |
| B | Asn | Leu | Tyr | Tyr | His | Gln | 1 |
| C | Pro | Thr | Ser | Ser | Arg | Arg | 1 |
| D | Asp | Arg | Trp | Met | Asn | Pro | 2 |
| E | Leu | Cys | Gly | Cys | Phe | Ser | 1 |

>group A and B_deletion of module 5
>group C_deletion of module 5 and 6

Fig. 7

LRRV1　　　　　LRRV4 LRRVe CP

Intact module　Selected module　Randomized module

Fig. 8

LRRV1　　　　　LRRV4 LRRVe CP

Intact module　Selected module　Randomized module

POLYPEPTIDE BINDING TO EXTRACELLULAR DOMAIN OF EPIDERMAL GROWTH FACTOR RECEPTOR

CROSS-REFERENCE TO RELATED APPLICATIONS

This application is a U.S. national phase under the provisions of 35 U.S.C. § 371 of International Patent Application No. PCT/KR15/05079 filed May 21, 2015, which in turn claims priority of Korean Patent Application No. 10-2014-0062391 filed May 23, 2014. The disclosures of such international patent application and Korean priority patent application are hereby incorporated herein by reference in their respective entireties, for all purposes.

TECHNICAL FIELD

The present invention relates to a novel polypeptide that binds to the extracellular domain of epidermal growth factor receptor, and more particularly to a polypeptide capable of binding to the extracellular domain of epidermal growth factor receptor to inhibit the activity of the epidermal growth factor domain, a polynucleotide that encodes the polypeptide, and a method of producing the polypeptide using a recombinant microorganism having introduced therein an expression vector comprising the polynucleotide.

BACKGROUND ART

Antibody therapeutic agents show high efficacy and less side effects together in the treatment of various diseases compared to chemical agents, and thus have become the research objectives of global pharmaceutical companies and bioengineering companies. At present, a large number of antibody therapeutic agents are used in clinical applications, and many therapeutic agent candidates are under clinical trials.

However, despite such advantages, the antibody therapeutic agents have problems, including low tissue penetrability due to their large molecular weight, high product costs due to complicated production processes, and entry barriers created by existing patents. Due to such problems, artificial antibodies to replace the antibody therapeutic agents have recently been developed. Many studies have revealed that such artificial antibody scaffold proteins have an advantage over the antibody therapeutic agents in that they penetrate cancer tissue with greatly increased efficiency, suggesting that therapeutic effects of the artificial antibodies can be improved.

Under this background, the present inventors successfully developed a repebody which is a non-antibody protein scaffold capable of replacing existing antibodies. It was shown that the repebody had a size equal to about ⅕ of antibody, was produced in large amounts in E. coli, and showed little or no immunogenicity in animal studies. In addition, it was demonstrated that the repebody has very high thermal and pH stabilities, and its ability to bind to a target can be very easily increased to picomole levels, and its specificity for a target is very high (Korean Patent Application No. KR2013-0098089A).

Epidermal growth factor receptor (EGFR) is a disease inducer verified to be associated with colorectal cancer and a variety of cancers, and 90% or more of total colorectal cancer cases are known to be malignant tumors of epidermal origin. Overexpression and mutation of the EGFR are found in 50-90% or more of such cancers, and abnormalities in signal transduction systems by the EGFR are found commonly in the majority of cancers, and for this reason, the EGFR has been recognized as a major target in the development of anticancer agents. Furthermore, up to date, signal transduction systems through the EGFR are most clearly known compared to other signal transduction systems, and thus studies on the development of therapeutic agents that target the EGFR have been most actively conducted.

At present, drugs that target the extracellular domain of the EGFR include Cetuximab that is a chimeric monoclonal antibody drug. However, Cetuximab was reported to have low binding affinity and therapeutic effects compared to other monoclonal antibody drugs. In addition, it was reported to Cetuximab, when administered continuously, shows drug resistance, and causes side effects due to drug toxicity and side effects due to the chimeric antibody. To overcome such problems, it has been attempted to develop a new therapeutic method (such as multi-drug therapy) and new drugs (such as Nimotuzumab). Therefore, there is a need to develop EGFR-targeting therapeutic agents having a new concept, which overcome the limitations of existing drugs.

The present inventors successfully prepared a specific protein binder for various disease-related target proteins by use of the repebody scaffold, and verified through a cell-based method that the specific protein binder has biological inhibitory effects. However, studies on the application of the specific protein binder are still in the opening stage, and thus additional studies are required. In addition, the identification of lead substances, which bind to various receptors overexpressed in cancer cells, and the application thereof, have not yet been reported.

Under this background, the present inventors have screened a novel protein having a specific binding affinity for epidermal growth factor receptor (EGFR), based on a random mutation library constructed through analysis of the modularity (structural feature) and the overall structure of the repebody, in order to identify a protein that binds specifically to the extracellular domain of the EGFR, which is overexpressed in various cancers, by use of the repebody scaffold, and have found that the binding affinity of the protein can be increased by a method of increasing the affinity based on repeat modules, thereby completing the present invention.

DISCLOSURE OF INVENTION

Technical Problem

It is an object of the present invention to provide a polypeptide capable of binding strongly and specifically to epidermal growth factor receptor to inhibit the activity of the epidermal growth factor receptor.

Another object of the present invention is to provide a polynucleotide that encodes the polypeptide, and an expression vector comprising the polynucleotide.

Still another object of the present invention is to provide a recombinant microorganism having the expression vector introduced therein, and a method of producing the polypeptide by use of the recombinant microorganism.

Technical Solution

To achieve the above objects, the present invention provides a polypeptide which comprises an amino acid sequence of any one of SEQ ID NOS: 6 to 8 and is capable of effectively binding to epidermal growth factor receptor to inhibit the activity of the epidermal growth factor receptor.

The present invention also provides a polynucleotide that encodes the polypeptide, and a recombinant vector comprising the polynucleotide.

The present invention also provides a recombinant microorganism having introduced therein the polynucleotide or the recombinant vector.

The present invention also provides a method for producing a polypeptide, comprising the steps of: (i) culturing the recombinant microorganism to produce the polypeptide; and (ii) recovering the polypeptide from the cultured recombinant microorganism or the culture.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 shows modules selected to increase binding affinity in a third process. In this case, the sixth module was used in the construction of a library for increasing binding affinity.

FIG. 8 shows modules selected to increase binding affinity in a fourth process. In this case, the second module was used in the construction of a library for increasing binding affinity.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In order to develop a novel polypeptide capable of binding specifically to the extracellular domain of EGFR, the present inventors have constructed a library that randomly contains the repeat modules of a polypeptide that comprises a fusion of the N-terminus of internalin B protein and the leucine-rich repeat (LRR) protein domain of variable lymphocyte receptor (VLR). The polypeptide contained in the library may be encoded by a polynucleotide sequence of SEQ ID NO: 1 or a polynucleotide sequence having a homology of 75%, preferably 85%, more preferably 90%, further preferably 95% or more, with the polynucleotide sequence of SEQ ID NO: 1.

In addition, the library may be formed of phagemid including the polynucleotide. In the present invention, the term "phagemid" means a circular polynucleotide molecule derived from a phage which is a virus having *E. coli* as a host and includes sequences of proteins and surface-proteins required for propagation and proliferation. A recombinant phagemid may be produced using gene recombinant technology well known in the art, and site-specific DNA cleavage and connection may be performed by an enzyme, generally known in the art, and the like. The phagemid may include a signal sequence or leader sequence for secretion in addition to expression regulating factors such as a promoter, an operator, an initiation codon, a termination codon, an enhancer and may be mainly used in a method for labeling the protein on a surface of the phage by fusing a desired protein with a surface protein of the phage. The promoter of the phagemid is mostly inducible and may include a selective marker for selecting a host cell. For an object of the present invention, the phagemid may be a polynucleotide of SEQ ID NO: 2 of the prior Korean patent KR2013-0098089A, including MalEss, DsbAss or PelBss which is a signal sequence or a leader sequence for expressing and secreting the polynucleotide constructing the library, and including a histidine-tag for confirming expression of a recombinant protein on a surface of the phage, and a polynucleotide which encodes gp3 domain which is a kind of a surface protein of M13 phage for expression on the surface of the phage, but the present invention is not particularly limited thereto.

Figures 1, 2:
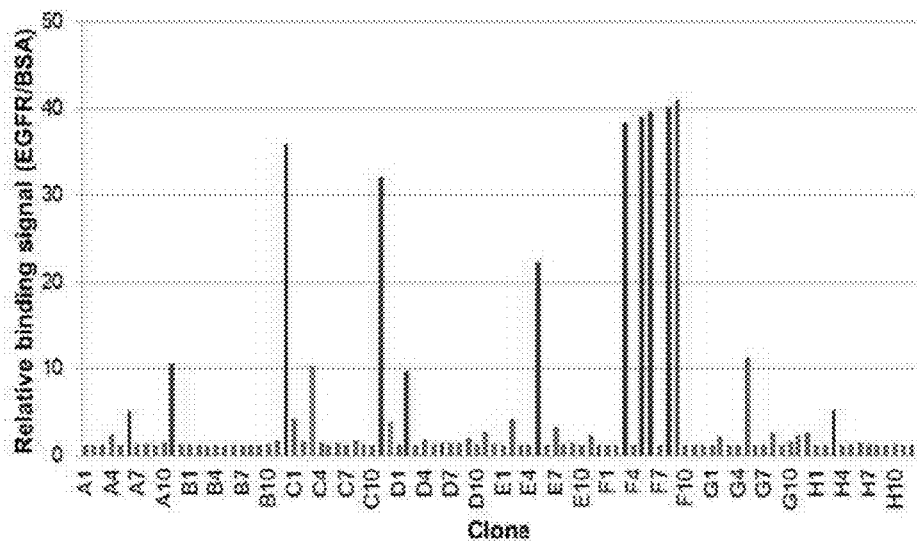
FIG. 1 shows the results of performing biopanning of phage display for the extracellular domain of EGFR by use of a phage library constructed according to a prior patent document (KR2013-0098089A). The signal of binding to the extracellular domain of EGFR relative to BSA, measured by enzyme-linked immunosorbent assay (ELISA), was normalized, and clones showing an increase in signal of three times or more were defined as repebody clones having specific binding affinity.
FIG. 2 shows the results of grouping the clones having specific binding affinity (shown in FIG. 1), based on modified amino acids. Each amino acid is located in the concave region of the repebody, a library for modules 3 and 4 was constructed.
Figure 3:
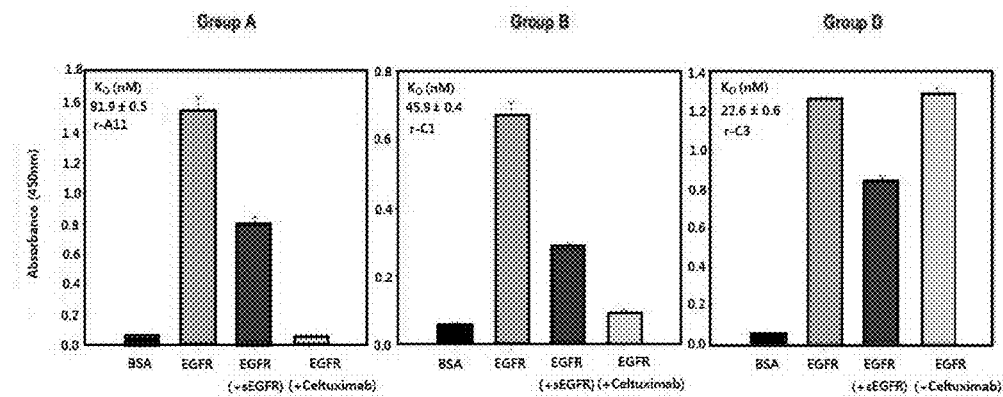
FIG. 3 shows the results of examining whether specific binding to the extracellular domain of EGFR occurs. The results are those obtained for three groups, and it can be seen that the clone binds specifically to the extracellular domain of EGFR without binding to BSA. Herein, it can be presumed that the clone showing a decrease in the ELISA signal due to Cetuximab introduced as a competitor is bound to the third domain of the extracellular domains of EGFR.
Figure 4:
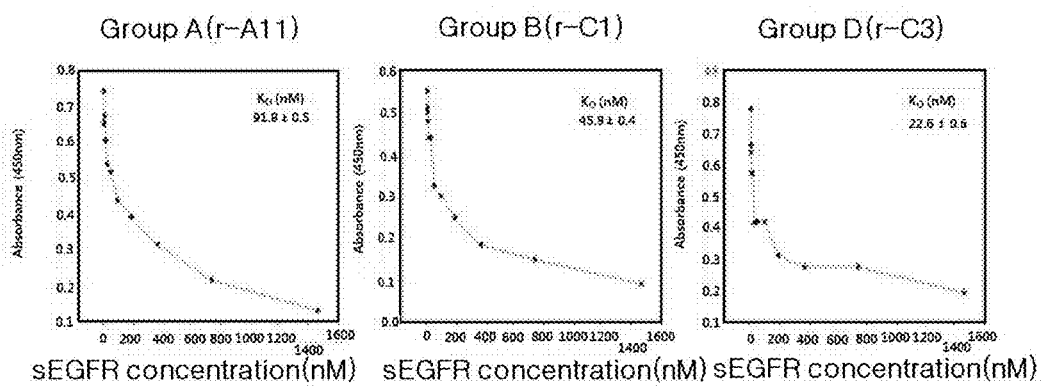
FIG. 4 shows the results of examining whether the binding of a repebody decreases in proportion to the concentration of the extracellular domain of water-soluble EGFR upon treatment of the extracellular domain in order to determine the apparent binding affinity of the repebody. Herein, the concentration of the extracellular domain of EGFR, at which the ELISA signal decreases 50%, was defined as dissociation constant.
Figure 5:
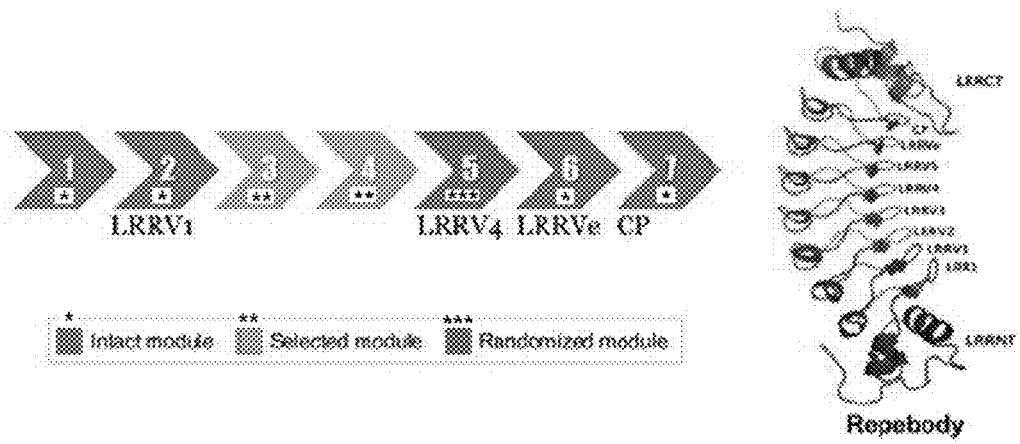
FIG. 5 shows modules selected to increase binding affinity in a second process. In this case, the fifth module was used in the construction of a library for increasing binding affinity. Herein, the green module indicates a position at which an existing library is constructed, and the red module indicates the corresponding position of a newly constructed library.

The present inventors have selected repebody-type novel polypeptides (SEQ ID NOs: 1 to 5) having high binding affinities for the extracellular domain of EGFR by use of a phage display method employing a library containing phagemids (FIGS. 1 and 2). However, these selected polypeptides have binding affinities for the extracellular domain of EGFR, which are lower than that for naturally occurring epidermal growth factor (EGF) (FIG. 3), and for this reason, mutation was applied to the selected polypeptides in order to construct mutated polypeptides having increased binding affinities for the extracellular domain of EGFR. For this, among the selected polypeptides, the polypeptide of SEQ ID NO: 2, confirmed to bind to the third domain of the extracellular domains of EGFR, was selected, and four amino acid residues located in the fifth module of the selected polypeptide were mutated to construct a second library (FIG. 4). Using a phage display method employing the second library, a novel polypeptide (SEQ ID NO: 6) having an increased binding affinity for the extracellular domain of EGFR was selected in the second round (FIG. 5).

Figure 6:
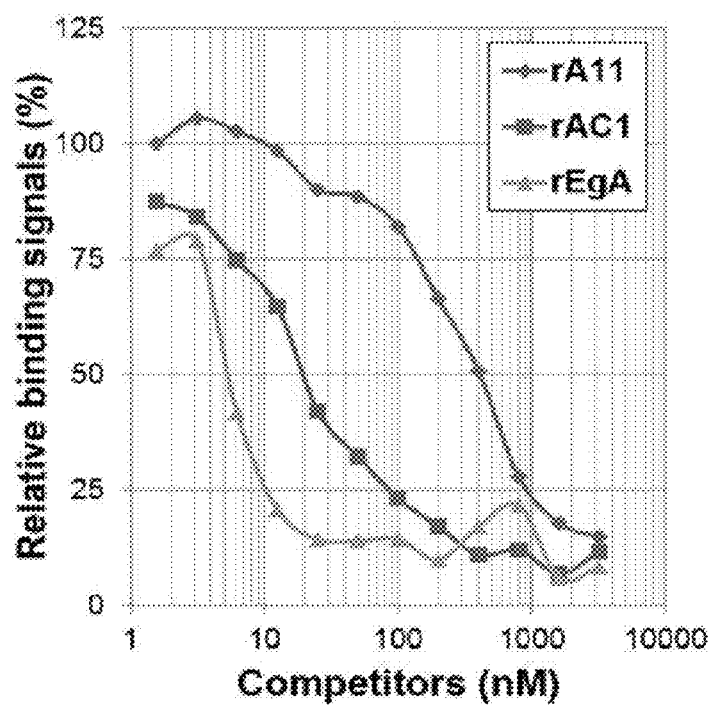
FIG. 6 shows the results of analyzing relative binding activity based on inhibition of the signal of binding to EGFR in ELISA while adding each repebody clone as a competitor in order to examine the binding affinity of phages having rA11 expressed on the surface. As the clone inhibited binding to the extracellular domain of EGFR at lower concentration, it was defined as a clone binding to the extracellular domain of EGFR with higher binding affinity.

Next, mutation of the polypeptide of SEQ ID NO: 6, which is a selected clone, was performed in the same manner to thereby construct a third library (FIG. 6). From the third library, a repebody-type novel polypeptide (SEQ ID NO: 7) having further increased binding activity for the extracellular domain of EGFR was selected in the third round by use of a phage display method. Finally, on the polypeptide selected in the third round, mutation was performed in the same manner to thereby construct a fourth library (FIG. 7). From the fourth library, a repebody-type polypeptide (SEQ ID NO: 8) having a binding affinity corresponding to a dissociation constant of pM was finally selected.

Therefore, in one aspect, the present invention is directed to a polypeptide comprising an amino acid sequence of any one of SEQ ID NOs: 6 to 8.

In the present invention, the term "internalin B protein" is a kind of the LRR family protein expressed in a *Listeria* strain, and it is known that the internalin B protein has an N-terminal structure different from that of the LRR family proteins in which a hydrophobic core are uniformly distributed through the entire molecule to thereby be stably expressed in microorganisms. It is considered that since the N-terminal of the internalin protein which is the most important in folding a repeat module is derived from a microorganism and has a stable shape including an alpha-helix, such that the internalin protein can be effectively used for stable expression of LRR family proteins in microorganisms.

In the present invention, the term "N-terminal of an (or the) internalin protein" of the present invention means an N-terminal of the internalin protein required for soluble expression and folding of the protein, and means a repeat module of the alpha-helix capping motif and the internalin protein. The N-terminal of the internalin protein may limitlessly include any N-terminal of the internalin protein required for soluble expression and folding of the protein, and as an example thereof, an alpha-helix capping motif "ETITVSTPIKQIFPDDAFAETIKANLKKKSVT-DAVTQNE" (SEQ ID NO: 9) and the repeat module may be included. The repeat module pattern may be "LxxLxxLx-LxxN" (SEQ ID NO: 10). In the repeat module pattern, L means alanine, glycine, phenylalanine, tyrosine, leucine, isoleucine, valine, or tryptophan; N means asparagine, glutamine, serine, cysteine or threonine; and x means any amino acid, e.g., any hydrophilic amino acid. In addition, the N-terminal of the internalin protein of the present invention may be selected and used as long as the N-terminal has a high structural similarity depending on a kind of the LRR family protein that can be fused, and the most stable amino acid may be selected by calculation of a binding energy, and the like, and the amino acid of the module corresponding thereto may be mutated.

As used herein, the term "epidermal growth factor receptor (EGFR)" refers to an about 170 KDa transmembrane protein which is present in the membrane of various cells and which is known to play an essential role in the growth, proliferation, migration and survival of cells. Cell proliferation signaling that is activated by the receptor causes abnormal cell proliferation by excessive dimerization of EGFR due to overexpression of epidermal growth factor (EGF) in cancer cells, and this phenomenon is found in various cancers such as lung cancer pancreatic cancer, breast cancer and colorectal cancer.

In the present invention, the term "repebody" is a polypeptide optimized by consensus design through fusion of the N-terminal of the internalin B having the LRR protein structure and the VLR based on the structural similarity. The repebody protein may be structurally divided into a concave region and a convex region (FIG. 4). Here, it is known that the concave region has high variety of the sequence and is important in protein interaction. On the contrary, the convex region serves to stably maintain the entire structure of protein based on the highly conserved sequence. The repebody protein may include all fusion LRR family protein obtained by using all proteins included in the LRR family having the repeat module to improve the solubility expression and biophysical properties of protein of all protein by the above-described method.

In the present invention, the term "variable Lymphocyte Receptor (VLR)" refers to a kind of the LRR family protein that is expressed and performs an immune function in hagfishes and lampreys, and is usefully used as a backbone capable of binding to various antigenic substances. A polypeptide in which the N-terminal of the internalin B protein and the VLR protein are fused is relatively increased in solubility and expression amount as compared to a VLR Protein that is not fused with the internalin B protein, and thus can be used in the preparation of a novel protein therapeutic agent based on the increase of solubility and expression amount.

As used herein, the term "Leucine rich repeat (LRR) family protein" means a protein formed by combination of modules in which leucine is repeated at a certain position, (i) it has one or more LRR repeat modules, (ii) the LRR repeat module consists of 20 to 30 amino acids, (iii) the LRR repeat module has "LxxLxxLxLxxN" as a conservation pattern, wherein L means hydrophobic aminoacids such as alanine, glycine, phenylalanine, tyrosine, leucine, isoleucine, valine, and tryptophan; N means asparagine, glutamine, serine, cysteine or threonine and x means any amino acid, and (iv) the LRR family protein means a protein having a three dimensional structure like horseshoe. The LRR family protein of the present invention may include all mutants having the sequence which is already known or found by mRNA or cDNA newly induced in vivo, as well as the sequence which is not known in the natural world through consensus design, and the like, and having a frame of the repeat module.

In another aspect, the present invention is directed to a polynucleotide that encodes the polypeptide, a recombinant vector comprising the polynucleotide, and a recombinant microorganism having the polynucleotide introduced therein.

As used herein, the term "vector" may be a DNA product containing base sequence of polynucleotide encoding a target protein operably linked to an appropriate regulation sequence so as to express the target protein in a suitable host cell. The regulation sequence may include a promoter capable of initiating transcription, an any operator sequence for regulating transcription, a sequence encoding an appropriate mRNA ribosome binding site, and a sequence regulating termination of transcription and decoding. The promoter of the vector may be constitutive or inducible. The vector may be transformed or transfected into a suitable host and then may be replicated or may perform functions regardless of the host genome, and may be integrated into a genome itself.

In the present invention, any vector which is known in the art may be used without any specific limitation as long as it can be replicated in the host. Examples of commonly used vectors include plasmid, cosmid, virus and bacteriophage in a natural state or a recombinant state. For example, pWE15, M13, λMBL3, λMBL4, λIXII, λASHII, λAPII, λt10, λt11, Charon4A, and Charon21A can be used as a phage vector or cosmid vector, and pBR-based, pUC-based, pBluescriptII-based, pGEM-based, pTZ-based, pCL-based and pET-based can be used as a plasmid vector. The vector which can be used in the present invention is not particularly limited and the known expression vectors can be used. Preferably, pACYC177, pACYC184, pCL, pECCG117, pUC19, pBR322, pMW118, pCC1BAC, pET-21a, pET-32a vectors can be used. Most preferably, pET-21a and pET-32a vectors can be used.

In the present invention, the term "recombinant microorganism" means a transfected cell in which a vector having polynucleotide encoding one or more target proteins is introduced into a host cell to express the target protein, and may include all cells including eukaryotic cells, prokaryotic cells, and the like. Examples thereof may include bacteria cells such as *E. coli, streptomyces, salmonella typhimurium*, and the like; yeast cells; fungus cells such as pichiapastoris, and the like; insect cells such as *drosophila, spodoptera* Sf9 cell, and the like; animal cells such as CHO, COS, NSO, 293, bow melanoma cell; and plant cells, but the present invention is not particularly limited thereto. A host cell that may be used in the present invention is not particularly limited, and *E. coli* may preferably be used as a host cell. Most preferably, *E. coli* BL21 (DE3) or OrigamiB (DE3) may be used as a host cell.

In the present invention, the term "transfection" means that a vector containing polynucleotide encoding a target protein is introduced into a host cell, or a polynucleotide encoding a target protein is integratedly completed into chromosome of the host cell, such that protein encoded by the polynucleotide is capable of being expressed in the host cell. The transfected polynucleotide may be any one regardless of the position as long as the polynucleotide is capable of being expressed in the host cell, regardless of the matter that the polynucleotide is inserted and positioned into chromosome of the host cell or positioned on an outer portion of the chromosome. In addition, the polynucleotide includes DNA and RNA encoding the target protein. The polynucleotide may be inserted with any type as long as the polynucleotide is capable of being introduced into the host cell to be expressed. For example, the polynucleotide may be introduced into the host cell as an expression cassette which is a gene structure, including all factors required for self expression. The expression cassette may include a promoter which is operably linked to the polynucleotide, a transcription termination signal, a ribosome binding site, and a translation termination signal. The expression cassette may be in the form of a self-replicable expression vector. In addition, the polynucleotide may be introduced into the host cell by itself and operably linked to the sequence necessary for expression in the host cell.

In still another aspect, the present invention is directed to a method for producing a polypeptide, comprising the steps of: (i) culturing the recombinant microorganism to produce the polypeptide; and (ii) recovering the polypeptide from the cultured recombinant microorganism or the culture.

In the method, the culturing of the recombinant microorganism may be preferably performed by a batch culture method, a continuous culture method, a fed-batch culture, and the like, known in the art, but the present invention not particularly limited thereto, wherein under the culture condition, pH may be appropriately adjusted (pH 5 to 9, preferably pH 6 to 8, most preferably pH 6.8) by using a basic compound (for example: sodium hydroxide, potassium hydroxide or ammonia) or an acidic compound (for example, phosphoric acid or sulfuric acid), and an aerobic condition may be maintained by introducing oxygen, or an oxygen-containing gas mixture into the culture, and the culture may be performed at 20 to 45° C., preferably, 25 to 40° C. for about 10 to 160 hours. The polypeptide produced by the culture may be secreted in the medium or remained in the cell.

In addition, in the culture medium used, as carbon source, sugar and carbohydrate (for example, glucose, sucrose, lactose, fructose, maltose, molasse, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing; as nitrogen source, nitrogen-containing organic compound (for example, peptone, yeast extract, gravy, malt extract, corn steep liquor, soybean meal powder and urea), or inorganic compound (for example, ammonium sulfate, ammonium chloride, ammonium phosphate, ammonium carbonate and ammonium nitrate) and the like, may be used individually or by mixing; as phosphate source, potassium dihydrogen phosphate, dipotassium hydrogen phosphate, sodium-containing salt corresponding thereof, and the like, may be used individually or by mixing; or essential growth-promoting materials such as other metal salts (for example, magnesium sulfate or iron sulfate), amino acids and vitamins may be included.

In the recovering of the polypeptide produced in the culturing of the present invention, the desired polypeptide may be recovered from a culture fluid by appropriate culture methods such as a batch culture method, a continuous culture method, a fed-batch culture, and the like, known in the art.

In yet another aspect, the present invention is directed to a composition for preventing or treating cancer, which comprises the polypeptide.

As used herein, the term "cancer" or "tumor" refers to a mass caused by the abnormal growth of body tissue. Because epidermal growth factor receptor (EGFR) is a growth factor that induces tumor proliferation and angiogenesis, the term "cancer" or "tumor" as used herein is meant to include all of colorectal cancer, non-small-cell lung cancer, ovarian cancer, multiple myeloma, Castleman's disease, liver cancer and the like, which secrete an excessive amount of epidermal growth factor receptor.

As used herein, the term "treating" refers to not only inhibiting or alleviating cancer or one or more symptoms caused thereby, but also treating cancer or preventing the progression of cancer, by administering the composition. As used herein, the term "preventing" refers to all actions that inhibit cancer or delay the onset of cancer by administering the composition.

In the present invention, the prevention or treatment of cancer is achieved by the binding of the polypeptide of the present invention to epidermal growth factor receptor. Specifically, cancer is prevented or treated by allowing the polypeptide to bind to the extracellular domain of epidermal growth factor receptor to significantly inhibit the activity of the epidermal growth factor domain.

A prior patent (KR10-1356075) to the present invention discloses that a novel repebody capable of binding interleukin-6 has a significant anticancer effect against non-small lung cancer. Thus, it is evident that a repebody of the present invention, which binds specifically to epidermal growth factor receptor, may also be used for the prevention or treatment of diseases caused by overexpression of epidermal growth factor receptor.

A composition for preventing or treating cancer, which comprises the polypeptide of the present invention, may further comprise a pharmaceutically acceptable carrier and may be formulated with a carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets.

A composition for preventing or treating cancer, which comprises the polypeptide of the present invention and a pharmaceutically acceptable carrier, can be applied as any formulation comprising it as an active ingredient and may be prepared as an oral or parenteral formulation. Pharmaceutical formulations of the present invention include those suitable for oral, rectal, nasal, topical (including buccal and sublingual), vaginal or parenteral (including intramuscular, subcutaneous and intravenous) administration or a form suitable for administration by inhalation or insufflation.

Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may include a binder such as lactose, saccharose, sorbitol, mannitol, starch, amylopectin, cellulose or gelatin, an expedient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

In a further aspect, the present invention is directed to a method for preventing or treating cancer, the method comprising administering the composition for preventing or treating cancer, which comprises the polypeptide.

As used herein, the term "administration" means introducing a desired material into a patient by any suitable method. The composition of the present invention may be administered through various routes such as an oral or parenteral route, as long as it can reach a desired tissue. For example, the composition of the present invention may be administered in a conventional manner via an oral, rectal, topical, intravenous, intraperitoneal, intramuscular, intravenous, transdermal, intranasal, inhalation, intraocular or intradermal route.

The treatment method of the present invention includes administering the composition for preventing or treating cancer of the present invention in a therapeutically effective amount. It is apparent to those skilled in the art that the suitable total daily dose of the composition can be determined by an attending physician or veterinarian within the scope of sound medical judgment. The specific therapeutically effective amount for any particular patient will depend upon various factors including the type and extent of response to be achieved, specific compositions according to whether other agents are used therewith or not, the patient's age, body weight, health condition, sex and diet, the time and route of administration, the secretion rate of the composition, the duration of treatment, other drugs used in combination or coincident with the composition, and other similar factors well-known in the medical field. Thus, the therapeutically effective amount of the composition for preventing or treating cancer, which is suitable for the purpose of the present invention, is preferably determined by taking into consideration the above-described factors.

In addition, the inventive method for treating cancer may be applied to any animal in which the excessive secretion of epidermal growth factor receptor may cause diseases including tumor development and angiogenesis. Examples of animals to which the inventive method may be applied include humans and primate mammals, as well as livestock animals such as cows, pigs, sheep, horses, dogs and cats.

Hereinafter, the present invention will be described in further detail with reference to examples. It will be obvious to a person having ordinary skill in the art that these examples are illustrative purposes only and are not to be construed to limit the scope of the present invention. In addition, it will be apparent to those skilled in that art that various modifications and variations can be made without departing from the technical scope of the present invention based on this illustration.

Example 1: Selection of Polypeptide Binding Specifically to Extracellular Domain of EGFR by Use of Random Phage Library A repebody phage library constructed according to Example 2 of a prior patent (KR2013-0098089A) was used as a component in the present invention. The phage library has mutations at a total of 6 amino acid positions, and also has mutations at the same positions as those shown in FIG. 5 of the prior patent (KR2013-0098089A).

Example 1-1: Selection of Polypeptide Binding to Extracellular Domain of EGFR by Panning of Repebody Library From the library constructed according to the prior patent (KR2013-0098089A), polypeptides capable of binding to the extracellular domain of EGFR were selected and purified. In order to select candidates capable of binding to the extracellular domain of EGFR, the extracellular domain of EGFR was added to an immuno-tube at a concentration of 100/, and the immune-tube was coated at 4° C. for 12 hours. The coated immune-tube was washed three times with PBS, and blocked with a PBS solution (TPBSA) containing 1% BSA and 0.1% Tween 20 at 4° C. for 2 hours. Then, the purified phages were added to the coated immuno-tube at a concentration of $10^{12}$ cfu/ml, and incubated at room temperature for 2 hours. After completion of the incubation, the immune-tube was washed five times with a PBS solution (TPBS) containing 0.1% Tween 20 for a total of 2 minutes and twice with PBS. Finally, 1 ml of 0.2 M Gly-HCl (pH 2.2) was added to the immune-tube, and incubated at room temperature for 10 minutes, thereby eluting phages in which repebody candidates capable of the extracellular domain of EGFR were expressed on the surface. The eluate was neutralized by adding 60 of 1.0M Tris-HCl (pH 9.1), and added to 10 ml of *E. coli* XL1-Blue (host cell)-containing solution (OD600=0.5), and then plated on a 2× YT plate. This bio-panning process was repeated 4 times in the same manner as described above. As a result, through each panning process, it was found that phages binding specifically to the extracellular domain of EGFR were concentrated. This result suggests that library phages binding to the extracellular domain of EGFR specifically increase.

Example 1-2: Confirmation of Whether Selected Repebodies Bind Specifically to EGFR and Sequencing of the Selected Repebodies The phages selected by the method of Example 1-1 were subjected to ELISA using 96-well plates coated with the extracellular domain of EGFR and BSA, thereby selecting 17 repebody candidates in which the absorbance (OD450) of the extracellular domain of EGFR was at least three times higher than that of BSA (FIG. 1). The amino acid sequence of each of the selected candidate was analyzed, and then clones having the same amino acid sequence were grouped. As a result, among the amino acid sequences of proteins binding specifically to the extracellular domain of EGFR expressed in the selected phages, the sequences of a total of five polypeptide groups (A to E) having the same amino acid sequence were identified. Specifically, it was shown that the amino acid isoleucine at position 126 was substituted with methionine, asparagines, proline or asparaginic acid, the amino acid threonine at position 128 was substituted with histidine, leucine, arginine or cysteine, the amino acid glycine at position 129 was substituted with tyrosine, serine or tryptophan, the amino acid valine at position 150 was substituted with tyrosine, serine, methionine or cysteine, the amino acid valine at position 152 was substituted with serine, histidine, arginine, asparagine or phenylalanine, and the amino acid glutamic acid at position 153 was substituted with glutamine, arginine, proline or serine (FIG. 2).

Such results suggest that residues playing an important role in binding to the extracellular domain of EGFR are present.

Example 1-3: Confirmation of Whether Selected Repebodies Bind to Third Extracellular Domain of EGFR It is very important to select a repebody binding to the third extracellular domain of EGFR from among the repebodies binding to the extracellular domain of EGFR, obtained in Example 1-1. It was widely reported that EGFR is overexpressed in many cancers, but mutation of EGFR itself also frequently occurs. For the general purpose use of a strategy that treats cancer by targeting the extracellular domain of EGFR with a monoclonal antibody, binding to the extracellular domain of EGFR from which the first and second domains were removed by mutation should also be possible. Thus, many inventors have developed and selected polypeptides capable of binding mainly to the third domain in order to obtain an effective ability to target the extracellular domain of EGFR.

Under this background, among the five individual polypeptides obtained in Example 1-2, rA11 (SEQ ID NO: 1), rC1 (SEQ ID NO: 2) and rC3 (SEQ ID NO: 4), which are representative clones corresponding to groups A, B and D, respectively, were used to perform ELISA. As a result, it was shown that all the three clones did not bind to BSA, but had the ability to bind specifically to the extracellular domain of EGFR (FIG. 3). In addition, the extracellular domain of water-soluble EGFR (soluble EGFR) was added to plates coated with the extracellular domain of EGFR, and as a result, it was shown that the ELISA signal was reduced, suggesting that the selected repebodies effectively bind to the extracellular domain of EGFR even in the aqueous solution phase. Finally, competitive ELISA with the monoclonal antibody Cetuximab known to bind to the third domain of EGFR was performed, and as a result, it was shown that, in all the representative clones A and B excluding clone D, the binding signal was reduced by Cetuximab, suggesting that the corresponding clones bind specifically to the third extracellular domain of EGFR (FIG. 3).

Example 2: Increase in Binding Affinity of Repebody for Extracellular Domain of EGFR by Module-Based Method As a component of the present invention, a module-based method of increasing affinity as described in the above-mentioned prior patent was performed. The module-based method is a technique that can generally be used for proteins having repeat modules, and was successfully reproduced in the present invention to enable the design of proteins having a high level of affinity.

Example 2-1: Construction of Additional Libraries by Use of Modules and Confirmation of Increase in Affinity The results of Example 1-3 indicated that the clone rA11 can most effectively bind to the third domain of EGFR. The clone rA11 has a dissociation constant of 92 nM for the extracellular domain of EGFR (FIG. 4), but monoclonal antibodies that are used in most anticancer therapies are used as effective targeted therapeutic agents with a binding affinity corresponding to a dissociation constant of several nM or several hundred pM. Thus, it was thought that the repebody candidates of the present invention cannot sufficiently inhibit the activity of EGFR.

In order to solve this problem, it was attempted to develop a mutant having increased binding affinity by use of a method of constructing additional libraries using modules as described in Example 4 of the prior patent (KR2013-0098089A).

Specifically, four residues in the concave region of the repebody were mutated in the same manner as described in Example 4-2 of the prior patent (KR2013-0098089A) (FIG. 5). Specifically, the fifth module of the first library for increasing affinity based on modules was mutated, and the library was subjected to a total of four panning processes, thereby obtaining rAC1 (SEQ ID NO: 6) having increased binding affinity. The results of ELISA indicated that rAC1 inhibited the binding of rA11 to the extracellular domain of EGFR at a concentration lower than that of rA11 (FIG. 6).

Figure 9:
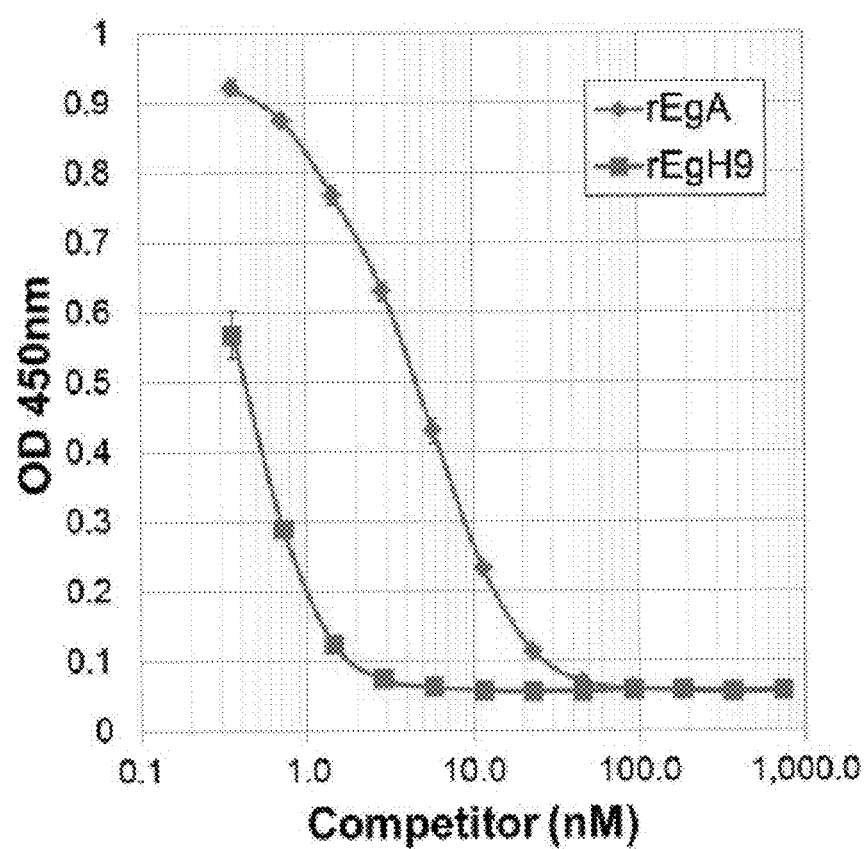
FIG. 9 shows the results of an ELISA experiment performed to examine the relative binding affinity of the final repebody clone rEgH9 in the same manner as shown in FIG. 6.

Meanwhile, in order to develop a mutant having further increased binding affinity, using rAC1 as a basic polypeptide, four residues in the sixth module adjacent to the fifth module were mutated (FIG. 7), and then the library was subjected to the same panning processes, thereby selecting rEgA (SEQ ID NO: 7). The results of ELISA indicated that rEgA had a binding affinity higher than that of rAC1 (FIG. 6). In a third process for increasing binding affinity, a library corresponding to four residues of the second module was constructed based on rEgA, and as a result, the clone rEgH9 (SEQ ID NO: 8) having increased binding affinity compared to rEgA could be successfully obtained (FIGS. 8 and 9).

Figure 10:
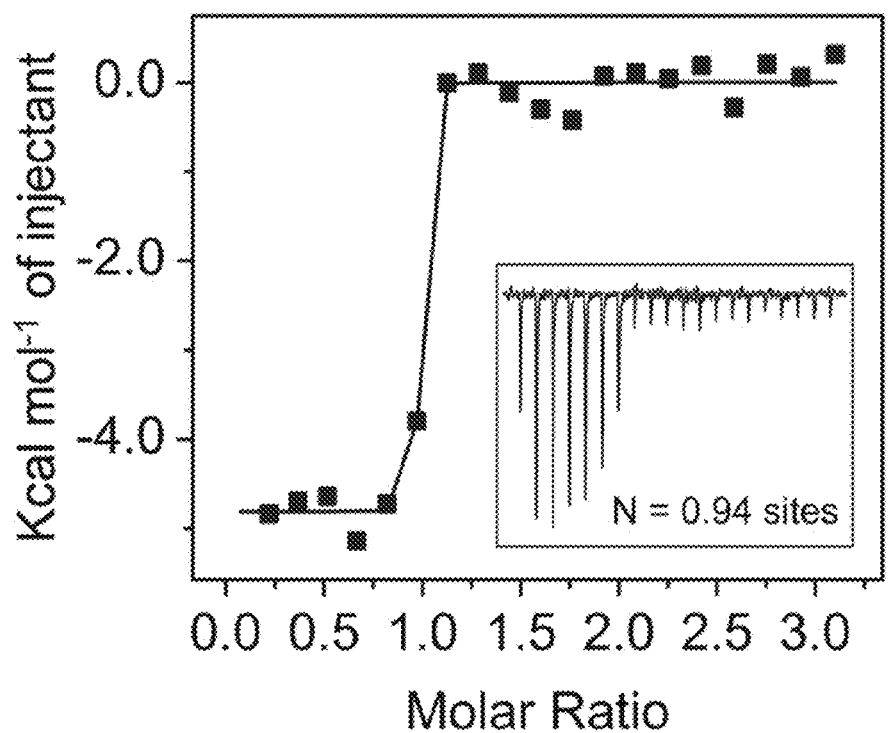
FIG. 10 shows the results of measuring the dissociation constant of rEgH9 showing the highest binding affinity, obtained in the present invention, by isothermal titration calorimetry (ITC), and indicates that rEgH9 has a high binding affinity for the extracellular domain of EGFR, which corresponds to a dissociation constant of 200 pM.

Meanwhile, the dissociation constant of the repebody rEgH9 clone for the extracellular domain of EGFR was measured. Specifically, the repebody dissolved in PBS at a concentration of 0.3 mM (6 mg/ml), and the extracellular domain of EGFR dissolved in PBS at a concentration of 0.02 mM (1.4 mg/ml), were used, and the dissociation constant of rEgH9 for the extracellular domain of EGFR at 37° C. was measured using isothermal titration calorimetry (ITC) (FIG. 10). FIG. 10 shows the results of measuring the binding affinity of the polypeptide of the present invention for the extracellular domain of EGFR by use of isothermal titration calorimetry. As shown in FIG. 10, the dissociation constant of the final clone rEgH9 for the extracellular domain of EGFR was 301 pM, indicating that the clone rEgH9 could very strongly bind to the extracellular domain of EGFR. Accordingly, the clone rEgH9 was obtained as a final clone.

Based on the above-described results, the present inventors have successfully obtained a repebody having a high level of binding affinity comparable to those of a variety of monoclonal antibodies that are used as effective targeted therapeutic agents, and have found that the repebody is a polypeptide having a specific binding affinity for the extracellular domain of EGFR.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the polypeptide of the present invention can bind to the extracellular domain of EGFR with a high binding affinity comparable to those of monoclonal antibodies that are widely used as targeted therapeutic agents, thereby inhibiting the activity of the EGFR. Thus, the polypeptide of the present invention is useful for the development of agents for the prevention or treatment of EGFR-related diseases.

The invention claimed is:

1. A polypeptide which has the ability to bind specifically to epidermal growth factor receptor protein and comprises the amino acid sequence of any one of SEQ ID NOS: 6 to 8.

2. The polypeptide of claim 1, wherein the polypeptide has the ability to bind to the extracellular domain of epidermal growth factor receptor to inhibit the activity of the epidermal growth factor domain.

3. A polypeptide which has the ability to bind specifically to epidermal growth factor receptor protein and comprises the amino acid sequence of any one of SEQ ID NOS: 6 to 8,
wherein the polypeptide comprises a fusion of the N-terminus of internalin B protein, a modified repeat module of variable lymphocyte receptor (VLR) protein, and the C-terminus of the VLR protein.

4. A polypeptide which has the ability to bind specifically to epidermal growth factor receptor protein and comprises the amino acid sequence of any one of SEQ ID NOS: 6 to 8,
wherein the modified repeat module of the VLR protein comprises the following repeat module pattern:
LxxLxxLxLxxN (SEQ ID NO: 10)
wherein L is alanine, glycine, phenylalanine, tyrosine, leucine, isoleucine, valine, or tryptophan, N is asparagine, glutamine, seine, cysteine, or threonine, and x is any one of all 20 amino acids.

5. A polynucleotide that encodes the polypeptide of claim 1.

6. A recombinant vector comprising the polynucleotide of claim 5.

7. A recombinant microorganism having introduced therein the polynucleotide of claim 5.

8. A recombinant microorganism having introduced therein the polynucleotide of claim 6.

9. A method for producing a polypeptide binding specifically to epidermal growth factor receptor protein, comprising the steps of:
(i) culturing the recombinant microorganism of claim 7 to produce a polypeptide which has the ability to bind specifically to epidermal growth factor receptor protein and comprises an amino acid sequence of any one of SEQ ID NOS: 6 to 8; and
(ii) recovering the polypeptide of claim 1 from the cultured recombinant microorganism or the culture.

10. A composition for preventing or treating cancer, which comprises the polypeptide of claim 1.

11. The composition of claim 10, wherein the prevention or treatment of cancer is achieved by the binding of the polypeptide to epidermal growth factor receptor.

* * * * *

SEQUENCE LISTING

```
<160> NUMBER OF SEQ ID NOS: 10

<210> SEQ ID NO 1
<211> LENGTH: 242
<212> TYPE: PRT
<213> ORGANISM: Artificial Sequence
<220> FEATURE:
<223> OTHER INFORMATION: rA11 polypeptide

<400> SEQUENCE: 1

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Met Leu His Tyr Asn Gln
                85                  90                  95

Leu Gln Ile Leu Pro Asn Gly Val Phe Asp Lys Leu Thr Asn Leu Lys
```

```
            100               105               110
Glu Leu Tyr Leu Ser Glu Asn Gln Leu Gln Ser Leu Pro Asp Gly Val
            115               120               125

Phe Asp Lys Leu Thr Asn Leu Thr Glu Leu Asp Leu Ser Tyr Asn Gln
            130               135               140

Leu Gln Ser Leu Pro Glu Gly Val Phe Asp Lys Leu Thr Gln Leu Lys
145               150               155               160

Asp Leu Arg Leu Tyr Gln Asn Gln Leu Lys Ser Val Pro Asp Gly Val
                165               170               175

Phe Asp Arg Leu Thr Ser Leu Gln Tyr Ile Trp Leu His Asp Asn Pro
            180               185               190

Trp Asp Cys Thr Cys Pro Gly Ile Arg Tyr Leu Ser Glu Trp Ile Asn
            195               200               205

Lys His Ser Gly Val Val Arg Asn Ser Ala Gly Ser Val Ala Pro Asp
            210               215               220

Ser Ala Lys Cys Ser Gly Ser Gly Lys Pro Val Arg Ser Ile Ile Cys
225               230               235               240

Pro Thr

<210> SEQ ID NO 2
<211> LENGTH: 242
<212> TYPE: PRT
<213> ORGANISM: Artificial Sequence
<220> FEATURE:
<223> OTHER INFORMATION: rC1 polypeptide

<400> SEQUENCE: 2

Glu Thr Ile Thr Val Ser Thr Pro Ile Lys Gln Ile Phe Pro Asp Asp
1               5                 10                15

Ala Phe Ala Glu Thr Ile Lys Ala Asn Leu Lys Lys Lys Ser Val Thr
            20                25                30

Asp Ala Val Thr Gln Asn Glu Leu Asn Ser Ile Asp Gln Ile Ile Ala
            35                40                45

Asn Asn Ser Asp Ile Lys Ser Val Gln Gly Ile Gln Tyr Leu Pro Asn
50                55                60

Val Arg Tyr Leu Ala Leu Gly Gly Asn Lys Leu His Asp Ile Ser Ala
65                70                75                80

Leu Lys Glu Leu Thr Asn Leu Thr Tyr Leu Asn Leu Leu Tyr Asn Gln
                85                90                95

Leu Gln Ser Leu Pro Asn Gly Val Phe Asp Lys Leu Thr Asn Leu Lys
            100               105               110

Glu Leu Tyr Leu His Gln Asn Gln Leu Gln Ser Leu Pro Asp Gly Val
            115               120               125

Phe Asp Lys Leu Thr Asn Leu Thr Glu Leu Asp Leu Ser Tyr Asn Gln
            130               135               140

Leu Gln Ser Leu Pro Glu Gly Val Phe Asp Lys Leu Thr Gln Leu Lys
145               150               155               160

Asp Leu Arg Leu Tyr Gln Asn Gln Leu Lys Ser Val Pro Asp Gly Val
                165               170               175

Phe Asp Arg Leu Thr Ser Leu Gln Tyr Ile Trp Leu His Asp Asn Pro
            180               185               190

Trp Asp Cys Thr Cys Pro Gly Ile Arg Tyr Leu Ser Glu Trp Ile Asn
            195               200               205

Lys His Ser Gly Val Val Arg Asn Ser Ala Gly Ser Val Ala Pro Asp
            210               215               220
```

```
Ser Ala Lys Cys Ser Gly Ser Gly Lys Pro Val Arg Ser Ile Ile Cys
225                 230                 235                 240

Pro Thr

<210> SEQ ID NO 3
<211> LENGTH: 218
<212> TYPE: PRT
<213> ORGANISM: Artificial Sequence
<220> FEATURE:
<223> OTHER INFORMATION: 1-2 Group C polypeptide

<400> SEQUENCE: 3

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Pro Leu Thr Ser Asn Gln
                85                  90                  95

Leu Gln Ser Leu Pro Asn Gly Val Phe Asp Lys Leu Thr Asn Leu Lys
            100                 105                 110

Glu Leu Ser Leu Arg Arg Ile Asn Cys Ser Leu Cys Arg Met Gly Val
        115                 120                 125

Phe Asp Lys Leu Thr Gln Leu Lys Asp Leu Arg Leu Tyr Gln Asn Gln
130                 135                 140

Leu Lys Ser Val Pro Asp Gly Val Phe Asp Arg Leu Thr Ser Leu Gln
145                 150                 155                 160

Tyr Ile Trp Leu His Asp Asn Pro Trp Asp Cys Thr Cys Pro Gly Ile
                165                 170                 175

Arg Tyr Leu Ser Glu Trp Ile Asn Lys His Ser Gly Val Val Arg Asn
            180                 185                 190

Ser Ala Gly Ser Val Ala Pro Asp Ser Ala Lys Cys Ser Gly Ser Gly
        195                 200                 205

Lys Pro Val Arg Ser Ile Ile Cys Pro Thr
    210                 215

<210> SEQ ID NO 4
<211> LENGTH: 266
<212> TYPE: PRT
<213> ORGANISM: Artificial Sequence
<220> FEATURE:
<223> OTHER INFORMATION: rC3 polypeptide

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60
```

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Asp Leu Arg Trp Asn Gln
            85                  90                  95

Leu Gln Ser Leu Pro Asn Gly Val Phe Asp Lys Leu Thr Asn Leu Lys
            100                 105                 110

Glu Leu Met Leu Asn Pro Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
            165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 5
<211> LENGTH: 266
<212> TYPE: PRT
<213> ORGANISM: Artificial Sequence
<220> FEATURE:
<223> OTHER INFORMATION: 1-2 Group E polypeptide

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Leu Leu Cys Gly Asn Gln
            85                  90                  95

Leu Gln Ser Leu Pro Asn Gly Val Phe Asp Lys Leu Thr Asn Leu Lys
            100                 105                 110

Glu Leu Cys Leu Phe Ser Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 6
<211> LENGTH: 242
<212> TYPE: PRT
<213> ORGANISM: Artificial Sequence
<220> FEATURE:
<223> OTHER INFORMATION: rAC1 polypeptide

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Met Leu His Tyr Asn Gln
                85                  90                  95

Leu Gln Ile Leu Pro Asn Gly Val Phe Asp Lys Leu Thr Asn Leu Lys
            100                 105                 110

Glu Leu Tyr Leu Ser Glu Asn Gln Leu Gln Ser Leu Pro Asp Gly Val
        115                 120                 125

Phe Asp Lys Leu Thr Asn Leu Thr Glu Leu Asp Leu Ala Arg Asn Gln
    130                 135                 140

Leu Gln Ser Leu Pro Lys Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

```
<210> SEQ ID NO 7
<211> LENGTH: 242
<212> TYPE: PRT
<213> ORGANISM: Artificial Sequence
<220> FEATURE:
<223> OTHER INFORMATION: rEgA polypeptide

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Met Leu His Tyr Asn Gln
                85                  90                  95

Leu Gln Ile Leu Pro Asn Gly Val Phe Asp Lys Leu Thr Asn Leu Lys
            100                 105                 110

Glu Leu Tyr Leu Ser Glu Asn Gln Leu Gln Ser Leu Pro Asp Gly Val
        115                 120                 125

Phe Asp Lys Leu Thr Asn Leu Thr Glu Leu Asp Leu Ala Arg Asn Gln
    130                 135                 140

Leu Gln Ser Leu Pro Lys Gly Val Phe Asp Lys Leu Thr Gln Leu Lys
145                 150                 155                 160

Asp Leu Arg Leu Tyr Glu Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 8
<211> LENGTH: 242
<212> TYPE: PRT
<213> ORGANISM: Artificial Sequence
<220> FEATURE:
<223> OTHER INFORMATION: rEgH9 polypeptide

<400> SEQUENCE: 8

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60
```

```
Val Arg Met Leu His Leu Pro Ser Asn Lys Leu His Asp Ile Ser Ala
 65                  70                  75                  80

Leu Lys Glu Leu Thr Asn Leu Thr Tyr Leu Met Leu His Tyr Asn Gln
             85                  90                  95

Leu Gln Ile Leu Pro Asn Gly Val Phe Asp Lys Leu Thr Asn Leu Lys
            100                 105                 110

Glu Leu Tyr Leu Ser Glu Asn Gln Leu Gln Ser Leu Pro Asp Gly Val
        115                 120                 125

Phe Asp Lys Leu Thr Asn Leu Thr Glu Leu Asp Leu Ala Arg Asn Gln
    130                 135                 140

Leu Gln Ser Leu Pro Lys Gly Val Phe Asp Lys Leu Thr Gln Leu Lys
145                 150                 155                 160

Asp Leu Arg Leu Tyr Glu Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 9
<211> LENGTH: 39
<212> TYPE: PRT
<213> ORGANISM: Artificial Sequence
<220> FEATURE:
<223> OTHER INFORMATION: alpha-helix capping motif

<400> SEQUENCE: 9

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu
        35

<210> SEQ ID NO 10
<211> LENGTH: 12
<212> TYPE: PRT
<213> ORGANISM: Artificial Sequence
<220> FEATURE:
<223> OTHER INFORMATION: internalin repeat module
<220> FEATURE:
<221> NAME/KEY: MISC_FEATURE
<222> LOCATION: (1)..(1)
<223> OTHER INFORMATION: Xaa can be any of Ala, Gly, Phe, Tyr, Leu, Ile,
      Val, or Trp
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any of Ala, Gly, Phe, Tyr, Leu, Ile,
      Val, or Trp
```

```
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any of Ala, Gly, Phe, Tyr, Leu, Ile,
      Val, or Trp
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any of Ala, Gly, Phe, Tyr, Leu, Ile,
      Val, or Trp
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
<221> NAME/KEY: MISC_FEATURE
<222> LOCATION: (12)..(12)
<223> OTHER INFORMATION: Xaa can be any of Asn, Gln, Ser, Cys, or Thr

<400> SEQUENCE: 10

Xaa Xaa Xaa Xaa Xaa Xaa Xaa Xaa Xaa Xaa Xaa Xaa
1               5                   10
```